United States Patent [19]

DePasquale et al.

[11] Patent Number: 4,591,652
[45] Date of Patent: May 27, 1986

[54] POLYHYDROXYL SILANES OR SILOXANES

[75] Inventors: Ralph J. DePasquale; Michael E. Wilson, both of Jacksonville, Fla.

[73] Assignee: SCM Corporation, New York, N.Y.

[21] Appl. No.: 722,326

[22] Filed: Apr. 12, 1985

[51] Int. Cl.$^4$ ............................................... C07F 7/10
[52] U.S. Cl. ................................................. 556/419
[58] Field of Search ....................................... 556/419

[56] References Cited

U.S. PATENT DOCUMENTS

| | | | |
|---|---|---|---|
| 3,046,250 | 7/1962 | Plueddemann | 556/419 X |
| 3,432,536 | 3/1969 | Simoneau | 556/419 |
| 3,442,926 | 5/1969 | Houtman | 556/419 |
| 3,564,037 | 2/1971 | Delaval et al. | 556/419 X |
| 4,082,689 | 4/1978 | Heyden et al. | 556/419 X |

*Primary Examiner*—Paul F. Shaver
*Attorney, Agent, or Firm*—R. A. Sturges; T. M. Schmitz

[57] ABSTRACT

Polyhydroxyl silanes or siloxanes useful as vehicles for coatings applicable to metal, mineral or glass surfaces, are made by reacting a silane or siloxane having an amine terminated substituent attached to silicon with an aldonic acid lactone. Reaction occurs at temperatures below 80° C. in alcohol solution under inert gas blanket. Products are water soluble and polymerizable at slightly elevated temperatures to hard, water insoluble tightly adhering films.

10 Claims, No Drawings

POLYHYDROXYL SILANES OR SILOXANES

This invention relates to polyhydroxyl silanes or siloxanes and a method for making such silanes or siloxanes. The products are useful as vehicles for coatings on metal or glass.

BACKGROUND OF THE INVENTION

Water soluble, or hydrophilic silanes that are presently available generally contain amine, carboxylate, sulfonate, phosphonate, thiol, ether, epoxy or ureido groups in their structure. We are unaware of any silanes containing multiple hydroxyl groups and one or more amino or amido groups embedded in the molecule. The present invention concerns amine or amido, polyhydric substituted silanes.

BRIEF STATEMENT OF THE INVENTION

Briefly stated, the present invention is in a hydrophilic silane having the general formula:

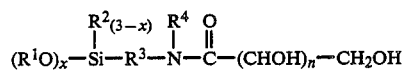   (I)

wherein $R^1$ and $R^2$ are independently selected from $C_1$-$C_3$ monovalent hydrocarbon radicals; $R^3$ is a divalent radical selected from $C_1$-$C_{12}$ hydrocarbon radicals, $-(CH_2)_3(NHCH_2CH_2)_{1-20}$,

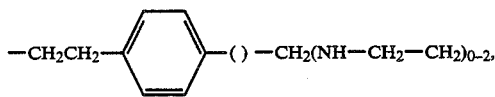

phenylene, and $R^4$ is selected from hydrogen, phenyl and $R^1$; x is 0, 1, 2, or 3 and n is an integer from 3 to 5.

These compounds contain, therefore, at least 4 hydroxyl groups on successive carbon atoms.

The process by which compounds of the above general formula are produced is by reacting substantially equimolar quantities of an amine terminated silane, preferably an amine terminated polyalkoxy silane, with an aldonic acid lactone in the presence of a lower alkanol ($C_1$-$C_3$) and preferably under an inert gas blanket. A preferred aldonic acid lactone is delta-gluconolactone. The water soluble products are useful to produce on moderate heating strongly adherent water resistant and solvent insoluble surface coatings for metals, glasses, clays, and various minerals and cellulosic materials.

DETAILED DESCRIPTION OF THE INVENTION AND SPECIFIC EXAMPLES

As indicated above, the compounds of this invention are hydrophilic silanes containing a substituent group attached to an aminoalkyl group which is in turn attached by a Si—C bond to a silicon atom. The terminal amino group is reacted with an aldonic acid lactone to yield a polyhydroxy silane derivative wherein the hydroxyl groups are attached to contiguous carbons. Because the aldonic acids are 4-hydroxyalkanoic acids they lactonize readily to form a five- or six-membered ring. The most stable lactones are those containing a 6-membered ring such as delta-gluconolactone CA Reg. No.: 90-80-2. Another lactone useful herein is delta-glucuronolactone, CA Reg. No.: 32449-92-6.

The aldonic acid lactones react with the terminal amino group of the silane to form an amide with a distally extending tail of monohydroxy substituted carbon atoms numbering 5 or 6 depending on the chain length of the parent polyhydroxy carboxylic acid, and the location of the hydroxyl group involved in the lactonization. The reaction has been found to proceed easily in alcohol solution, and desirably under a dry, inert gas atmosphere, e.g., nitrogen, argon, helium, etc. The alcohol may be methanol, ethanol, n-propanol, or isopropanol.

The amine terminated silane reactants are many. They are characterized by a hydrocarbylene group of from 1 to 30 carbon atoms. The hydrocarbylene group may consist of or comprise alkyl groups, aryl groups, such as phenylene, diphenylene, naphthylene, cycloaliphatic groups, etc., and mixed alkyl and aryl groups. The hydrocarbylene group may be segmented into a plurality of hydrocarbylene groups separated by —NH—, (secondary amino linkages), e.g., $-(CH_2)_m(NHC_2H_4)_n-NH$ where m is 1 to 4, and n is 1 to 20;

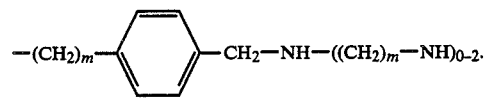

Also included in addition to silanes are siloxanes wherein $R^3$ is connected to an —Si—O—Si— group, the terminal silyl group being substituted in the same manner as the silyl group in the general formula (I) above and the silylene group being substituted with $C_1$-$C_3$ alkyl groups, e.g., methyl, ethyl or propyl.

It becomes convenient at this point to give specific illustrative of polyhydroxyl silanes and siloxanes in accordance with the present invention.

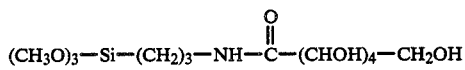   (II)

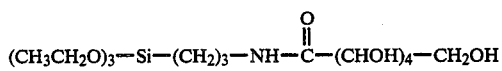   (III)

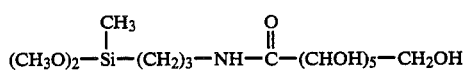   (IV)

-continued
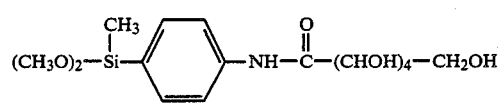 (V)
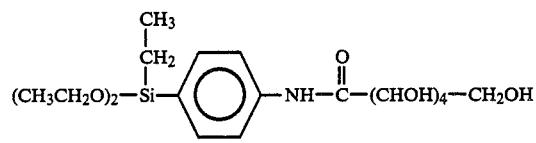 (VI)
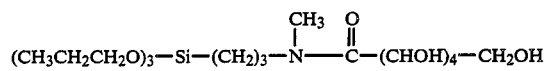 (VII)
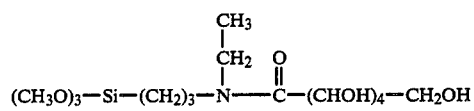 (VIII)
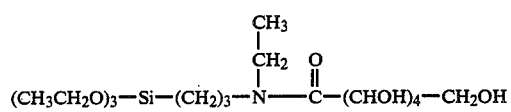 (IX)
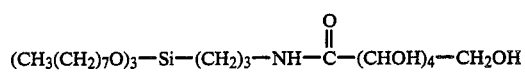 (X)
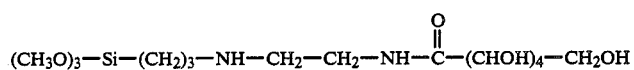 (XI)
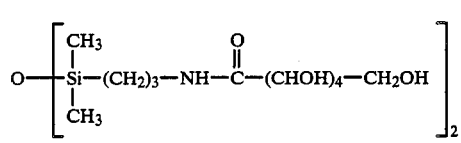 (XII)
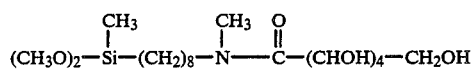 (XIII)
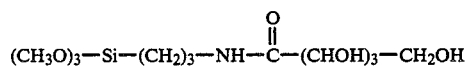 (XIV)
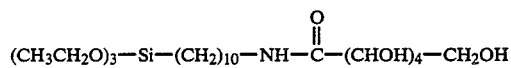 (XV)
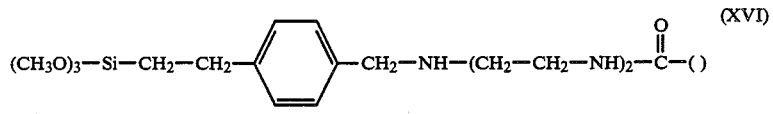 (XVI)
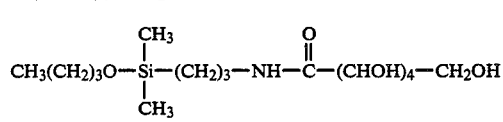 (XVII)
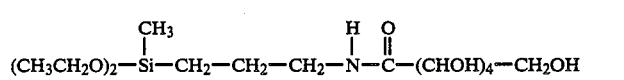 (XVIII)
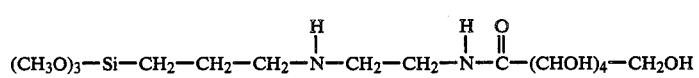 (XIX)
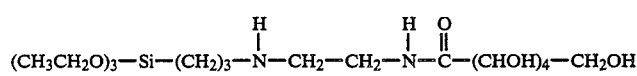 (XX)
These products are water soluble and provide vehicles soluble in water for coating various substrates including metal, e.g., steel, glass, and minerals. The vehicles are applied from an aqueous solution ranging from about 5% to about 15% solids. The vehicle solids are heat curable at relatively low temperatures (90° C. to 150° C.) to hard, clear, cold water and solvent insoluble protective coatings which are strongly adherent to the substrate. Some protective coatings are soluble in boiling water.

The foregoing compounds are prepared from silane or siloxane compounds in which at least one substituent attached to a silicon atom has a terminal —$NH_2$ or =NH group. Reaction is effected with an aldonic acid lactone in alcohol under an inert gas blanket. The alcohol medium is desirably anhydrous. The reaction proceeds at temperatures below about 80° C. and generally at room temperature and with stoichiometric quantities of the reactants. The resultant products are water soluble. Upon casting as a film on a substrate (metal or glass) and heating to 90°-150° C. for 10 to 60 minutes, a clear, hard, adherent, generally water and solvent insoluble coating is obtained.

The method of making the foregoing compounds is conveniently illustrated by the following examples.

EXAMPLE I

To a slurry of 44.5 g. (0.25 mole) of glucono-delta-lactone in 100 g. of absolute ethanol was added 55.3 g. (0.25 mole) of gamma-aminopropyl triethoxysilane in one portion. After stirring under nitrogen for 15 minutes, the solution was clear, pale yellow, and slightly warm. No change was observed in the solution after several weeks. Infrared analysis of the neat film showed strong amide bands at 1635 and 1540 $cm^{-1}$. NMR ($CDCl_3$) was roughly consistent with the structure (III) above. Evaporation of the solvent gave a hard water soluble glass. Dipping a glass slide into an aqueous solution of the product and drying the sample at 100° C. for 30 minutes produced a hard, clear, water and solvent insoluble coating on the glass.

EXAMPLE II

To a slurry of 17.8 g. (0.10 mole) of glucono-delta-lactone in 100 ml. absolute methanol at room temperature were added 22.2 g. (0.10 mole) of 2-(3-aminopropyl)aminoethyltriethoxy silane in one portion. After stirring for 2 minutes, the solution was warm and slightly cloudy. After 3 hours, the reaction mass had turned to a white paste. The white precipitate was separated by filtration, washed with 50 ml. methanol, and dried under vacuum. The resulting white solid (29 g.) was insoluble in methanol, but very soluble in water and hot acetic acid. It melted with decomposition at about 160° C. This product is represented as (XX) above. A glass slide treated with an aqueous solution as in Example II, produced a hard, water insoluble film. Infrared (nujol mull) 3300, 1645, 1530, 1170, 980 $cm^{-1}$; amide bands at 1645 and 1530 $cm^{-1}$ are strong. NMR($D_2O$) 0.7(br m; 2H), 1.7(br m; 2H), 2.5-3.0(br m; 4H), 3.31(S; 3H), 3.4(m; 2H), 3.6-4.2(m; 5H), 4.3(d; 1H), 4.7(S; 7H)ppm. The low amount of Si—$OCH_3$ at 3.31 ppm, however, is indicative that the product is a cyclic monomer or a polymer.

EXAMPLE III

To a slurry of 17.8 g (0.10 mole) of glucono-delta-lactone (GDL) in 37 g. of absolute ethanol were added 19.1 g. (0.10 mole) of 3-aminopropylmethyldiethoxysilane in one portion. After stirring under nitrogen for 1 hour, the solution was cloudy, pale yellow, and slightly warm. It was warmed briefly to reflux and allowed to cool to ambient temperature. After 5 hours, the reaction was a pale yellow milky emulsion that readily formed a clear, pale yellow solution when added to water. IR (neat film) 3320, 2970, 1640, 1535, 1255, 1080, 1045, 950, 880, 800 $cm^{-1}$. This is product XXVII above. Dipping a glass slide into an aqueous solution (10% solids) of the product and drying the sample at 100° C. for 30 minutes produced a hard, hydrophilic coating that dissolved in boiling water.

What is claimed is:

1. A hydrophilic silane having the general formula:

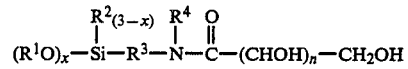

wherein $R^1$ and $R^2$ are independently selected from $C_1$-$C_3$ monovalent hydrocarbon radicals; $R^3$ is a divalent radical selected from $C_1$-$C_{12}$ hydrocarbon radicals; —$(CH_2)_3$—$(NHCH_2CH_2)$—$_{1-20}$;

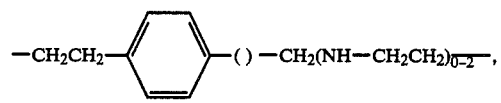

phenylene; $R^4$ is selected from hydrogen, $R^1$ and phenyl; x is 0, 1, 2, or 3, and n is an integer from 3 to 5.

2. A hydrophilic silane as defined in claim 1 wherein n is 4.

3. A hydrophilic silane as defined in claim 1 wherein $R^1$ is ethyl, x is 3, and $R^3$ is propylene.

4. A hydrophilic silane as defined in claim 1 wherein $R^1$ is methyl, x is 3 and $R^3$ is propylene.

5. A hydrophilic silane as defined in claim 1 wherein $R^1$ is ethyl, x is 3, $R^3$ is propylene and n is 4.

6. A hydrophilic silane as defined in claim 1 wherein $R^1$ is ethyl, x is 3, and $R^3$ is 2-(3-aminopropyl)amino ethyl.

7. A hydrophilic silane as defined in claim 6 wherein n is 4.

8. A process for making a hydrophilic silane having the general formula:

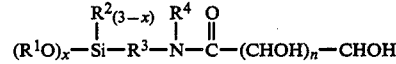

by reacting substantially equimolar quantities of a silane having the formula:

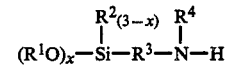

with an aldonic acid lactone in the presence of a lower alkanol and an inert atmosphere wherein $R^1$ and $R^2$ are independently selected from $C_1$-$C_3$ monovalent hydrocarbon radicals, $R^3$ is a divalent radical selected from $C_1$-$C_{12}$ hydrocarbon radicals; —$(CH_2)_3$—$(NHCH_2CH_2)$—$_{1-20}$;

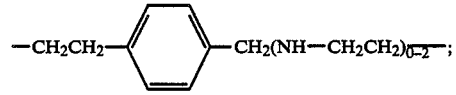

phenylene; $R^4$ is selected from hydrogen, $R^1$ and phenyl; x is 0-3 and n is 3-5.

9. A process as defined in claim 8 wherein the aldonic acid lactone is gluconolactone.

10. A process as defined in claim 8 wherein x is 3 and $R^1$ is lower alkyl.

* * * * *